United States Patent [19]

Martin et al.

[11] 4,044,404
[45] Aug. 30, 1977

[54] FIBRILLAR LINING FOR PROSTHETIC DEVICE

[75] Inventors: Graham Ernest Martin; Ian Derek Cockshott, both of Runcorn; Francis James Thomas Fildes, Macclesfield, all of England

[73] Assignee: Imperial Chemical Industries Limited, London, England

[21] Appl. No.: 600,942

[22] Filed: Aug. 1, 1975

[30] Foreign Application Priority Data

Aug. 5, 1974 United Kingdom ............... 34338/74

[51] Int. Cl.² ............................................ A61F 1/02
[52] U.S. Cl. ....................................... 3/19; 19/155; 128/156

[58] Field of Search .................. 128/155-157, 128/325, 334 R, DIG. 8, DIG. 22; 19/155; 3/19

[56] References Cited

U.S. PATENT DOCUMENTS

| | | | |
|---|---|---|---|
| 3,490,115 | 1/1970 | Owens et al. | 19/155 X |
| 3,556,969 | 1/1971 | Mizuguchi et al. | 128/DIG. 8 |
| 3,563,228 | 2/1971 | Seiderman | 128/DIG. 8 |
| 3,593,074 | 12/1971 | Isakoff | 19/155 |
| 3,600,717 | 8/1971 | McKeehan | 3/19 |
| 3,892,648 | 7/1975 | Phillips et al. | 128/DIG. 8 |

Primary Examiner—Lawrence W. Trapp
Attorney, Agent, or Firm—Cushman, Darby & Cushman

[57] ABSTRACT

A lining for a prosthetic device such as an artificial internal organ comprises a mat of fibres prepared by electrostatically spinning an organic material and collecting the spun fibres on a receiver.

17 Claims, 4 Drawing Figures

FIBRILLAR LINING FOR PROSTHETIC DEVICE

This invention relates to the production of fibrillar products by the electrostatic spinning of organic materials.

The technique of electrostatic spinning of liquids, including solutions containing a fibre-forming material is known and has been described in a number of patents as well as in the general literature.

The process of electrostatic spinning involves the introduction of a liquid into an electric field, whereby the liquid is caused to produce fibres which tend to be drawn to an electrode. While being drawn from the liquid the fibres usually harden, which may involve mere cooling (where the liquid is normally solid at room temperature, for example), chemical hardening (for example by treatment with a hardening vapour) or evaporation of solvent (for example of dehydration). The product fibres may be collected on a suitably located receiver and subsequently stripped from it.

The fibres obtained by the electrostatic spinning process are thin, of the oder of 0.1 to 25 micron, preferably 0.5 to 10 micron and more preferably 1.0 to 5 micron in diameter.

We have found that the fibres, if collected to form a mat of appropriate thickness may, because of the inherent porosity of the mat so obtained, provide a non-woven material having a wide variety of applications, depending upon the composition of the fibres, their density of deposition, their diameter, and their inherent strength, and the thickness and shape of the mat. It is also possible to post-treat such mats with other materials to modify their properties, for example to increase their strength or water resistance.

Fibres having different properties may be obtained by adjusting their composition either by spinning a liquid containing a plurality of components, each of which may contribute a desired characteristic to the finished product, or by simultaneously spinning from different liquid sources fibres of different composition which are simultaneously deposited to form a mat having an intimately intermingled mass of fibres of different material. A further alternative is to produce a mat having a plurality of layers of different fibres (or fibres of the same material but with different characteristics e.g. diameter) deposited, say, by varying with time the fibres being deposited upon the receiving surface. One way of effecting such a variation, for example, would be to have a moving receiver passing in succession sets of spinnerets from which fibres are being electrostatically spun, said fibres being deposited in succession as the receiver reaches an appropriate location relative to the spinnerets.

Thus, the present invention provides a mat comprising a plurality of fibres of organic material, said fibres being obtained by electrostatic spinning from a liquid comprising the material or a precursor thereof.

Within the term mat we include deposits of electrostatically spun fibres in the form of three dimensional as well as two dimensional articles.

The invention will be further understood from the following more detailed description taken with the drawings in which.

Figure 1:
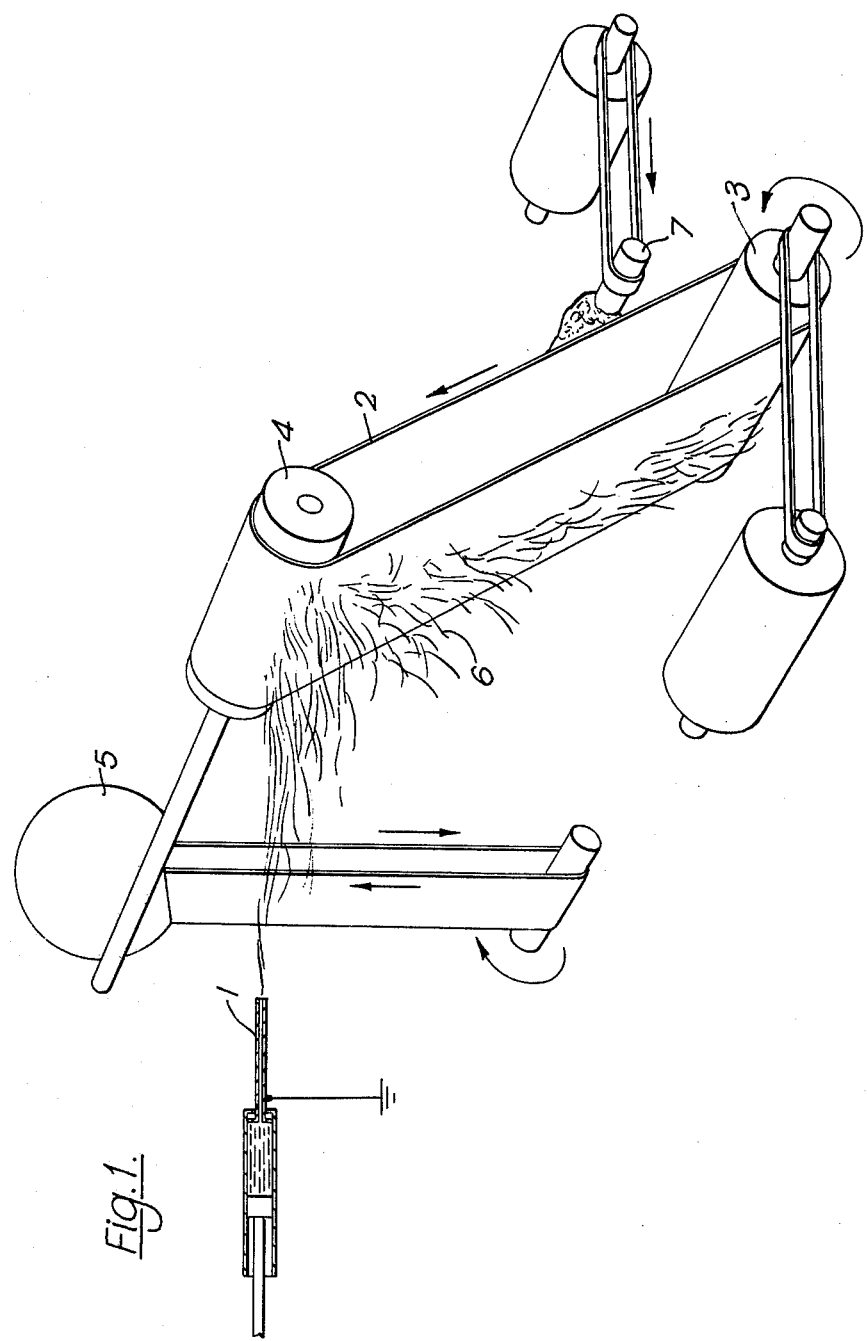
FIG. 1 is a schematic perspective view of an apparatus for electrostatically spinning and collecting fibres.

According to one embodiment of the present invention we provide a shaped mat of electrostatically spun fibres in a form appropriate for use as a wound dressing. A particular advantage of the use of materials made from the electrostatically spun fibres is that the fibres may be of very small diameter, to give a mat with small interstices and consequently a high surface area. Where the dressing is formed from a wettable polymer, blood or serum escaping from the wound tends to penetrate the dressing and the high surface area encourages clotting. Such dressings may be used as emergency dressings to halt bleeding. As examples of suitable polymers we may mention polyurethanes. Where the dressing is formed from a non-wetting polymer a particular advantage is that if the interstices between the fibres are sufficiently small, averaging, say 1 to 100 $\mu$, tissue fluids, including blood, tend not to permeate the dressing, so that the fluids are retained adjacent to the wound, where clotting will occur. Subsequent removal of such a dressing is facilitated by the absence of blood clot permeating the dressing material. Furthermore such dressings have the advantage that they are usually sufficiently porous to allow interchange of oxygen and water vapour between the atmosphere and the surface of the wound. As examples of suitable non-wetting polymers we may mention saturated polyesters e.g. polyethylene terephthalate, fluorinated compounds, particularly fluorinated hydrocarbons, e.g. PTFE, and silicones.

Such dressings may, of course, be associated with suitable supports or reinforcement, with mats of, say, woven fibres which may have other desirable properties, or with surface or other treatment with materials having antiseptic or wound-healing properties. Blood clotting, for example, may be encouraged by incorporating clotting accelerators or inducers in or on the mat and/or on materials associated therewith in a wound dressing. Other components with which the mat may be associated include water-proof layers intended to protect the mat from undesirable effects of moisture, dirt etc.

Preferably the wound dressing of the ivention comprises a mat of flexible non-absorbent, porous, hydrophobic material, together with a non-absorbent backing layer. Such a backing layer is preferably made of hydrophobic material, but this is not essential. The dressing may also include means for applying pressure to the mat such means may be, for example, a stretchable elastic bandage.

In a preferred embodiment the dressing comprises a backing layer, one surface of which has an adhesive facing, and on the same surface on the backing strip a porous mat of the material of the invention; optionally a pad of adsorbent or non-absorbent material is located between the backing layer and the mat.

Non-adherent dressings according to the invention have been tested for efficacy by applying them to a surface of a wound on a rabbit involving loss of an area of full thickness skin, and observing the progress of healing in comparison with control wounds. A dressing made from the preferred material allowed normal healing with little or no seepage of fluid through the dressing and minimal adherence of the dressing to the scab.

According to a further embodiment of the invention we provide a shaped mat comprising electrostatically spun fibres in the form of a lining or surfacing to a component which may be in contact with body fluids such as blood and lymph. Such mats may be tubular, or of irregular shape.

The difficulty of development of satisfactory blood and body tissue compatible surfaces on, say, the walls of artifical hearts and other circulatory assisting devices, as well as compatible linings to damaged natural as well as artificial blood vessels, represents an obstacle to the development of safe artificial organs and tissues. We have found that the deposition upon the surfaces of such artificial organs and tissues of a lining of thin fibres of appropriate material may improve their blood and other tissue fluid compatability. It is desirable for this purpose, however, that the lining is very thin and the use of an electrostatically deposited fibrous coating has been shown to meet many of the critical requirements. The primary desiderata include a. very small fibre diameters (small in relation to cell dimensions), so that fibre diameters of 0.1 micron to 10 micron, and particularly 0.5 to 5 micron are particularly appropriate.
b. The lining should be sufficiently porous to allow penetration of cells into it; ideally therefore the average pore dimension should be of the order of 5 to 25 micron, preferably 7 to 15 micron.
c. The lining should preferably be of the order of 10 to 50 micron in thickness.
d. The lining should be capable of being bonded to the article to which it constitutes a lining by some suitable means not involving a process destructive of the properties indicated above.
e. The lining should contain no materials harmful to the body or to the body cells or fluids which may come into contact with it.

The technique of electrostatic spinning provides a method of forming such linings to accord perfectly with the dimensions and contours of the articles to be coated by making the surface of the article or positive or negative replica thereof the collector in an electrostatic spinning process.

Materials suitable for the preparation of such linings include polymeric substances and in particular inert, polymeric substances. As preferred substances we would mention fluorinated hydrocarbons, e.g. PTFE which conveniently may be spun from a dispersion of the material in a suitable dispersing agent, and polyurethanes which may be spun from solution.

In some applications the mat may be strong enough, or may be spun thick enough, to be used without a supporting article i.e. it will not properly be described as a lining. Thus self-supporting tubular devices may be electrostatically spun; for example vascular prosthetics may be prepared from polytetrafluoroethylene or from polyurethanes, etc.

The electrostatically spun products, for example tubes or other shaped items, may be described above, be of sufficient strength to be employed as such, without reinforcement. However, it is usually preferred that the material is reinforced, for example by applying to one surface of the product a reinforcing layer, which itself may be electrostatically spun, or by incorporating reinforcement within the call of the product itself. Thus, we have reinforced electrostatically spun products by incorporating within the wall thereof a web which may be woven or non-woven, or an alternative arrangement of fibres. We particularly prefer to employ as reinforcement a helix of suitable fibre, said helix being located within the walls of a tubular product comprising electrostatically spun fibrous material. Although it is usual to enclose the reinforcement within the wall material we do not exclude the possibility of applying it to a surface of the product where its presence will not be disadvantageous. The thickness of reinforcement will be influenced inter alia by the thickness of the mat the location of the reinforcement and the reinforcement strength required. In general the thickness of the reinforcement will be less than that of the mat, although where the reinforcement lies at a surface of the mat and may project therefrom the thickness of the reinforcement may be thicker than that of the mat. Generally the thickness of the reinforcement (or of reinforcing fibres) will be of the order of 0.1 to 10 times the thickness of the mat preferably 0.2 to 0.8 times.

Suitable reinforcing materials include metallic, polymeric or glass fibre. Such electrostatically spun tubes and other prosthetics have the advantge over tubes used hitherto in this application in generating a thinner layer of encapsulating natural tissue so that smaller diameter tubes may be used without the tube becoming clogged by natural tissue.

The mats according to the present invention may be spun from a solution of or a dispersion of a polymer or its precursors. Polymers which may be conveniently spun from solution include high molecular weight fibre forming thermoplastics; in particular we would mention polyurethane, polyamides and polyacrylonitrile, Polymers which may conveniently be spun from dispersion include polytetrafluoroethylene and polyesters as well as those listed above. As an example of a polymer precursor which may be spun from solution we mention urea formaldehyde which may be cross-linked subsequent to spinning by treatment with acid vapour.

Water soluble polymers, e.g. polyvinyl alcohol, polyvinyl pyrrolidone, and polyethylene oxide, may be spun from aqueous solution. While we do not exclude the possibility that mats prepared from such materials may be used as prepared, preferably such mats are given at least a degree of insolubility in aqueous medium e.g. by cross-linking with a suitable regent.

Where the mats are spun from a dispersion the spinning material comprises preferably also a solution of an additional component which acts to enhance the viscosity of the suspension and to improve its fibre forming properties. Most convenient for this purpose, we have found, is an additional organic polymeric material which subsequent to fibre formation, can, if desired, be destroyed during sintering.

The preferred spinning material, then, is a solution or suspension which preferably comprises an organic polymer in an amount such that it is capable of forming a fibre and has cohesion properties such that the fibre form is retained during any post fibreization hardening until the fibre has hardened sufficiently not to lose its fibrous shape on detachment from a support where this is appropriate.

Where mats are spun from solution they comprise point bonded fibres and are often strong enough for use without any further treatment.

Where mats are spun from dispersion they often have a tendency to be friable, being mere agglomerations of discrete particles held together in the form of fibres by the additional organic polymeric component present. Preferably such mts are sintered so that the particles soften and flow into each other and the fibres may become point bonded. In the case of PTFE sintering may conveniently be carried out between 330° and 450° C, preferably between 370° and 390° C. Sterilisation may proceed concurrently during the sintering process. The sintering temperature in the case of PTFE is usually sufficiently high to destroy completely any undesirable organic component in the final product e.g. material added solely to enhance viscosity or emulsifying agent.

The additional organic component need be employed only in a relatively small proportion (usually within the range 0.001 to 12% and preferably 0.01 to 3%) by weight of the suspension, although the precise concentration for any particular application can easily be determined by trial.

The degree of polymerisation of the additional organic component is preferably greater than about 2000 units linearly; a wide range of such polymers is available. An important requirement is solubility of the polymer in the selected solvent or suspending medium which is preferably water. As examples of water-soluble polymeric compounds we may mention polyethylene oxide, polyacrylamide, polyvinyl pyrrolidone and polyvinyl alcohol; where an organic medium is employed to prepare the spinning material, either as the sole liquid solvent or as a component thereof, a further wide range of organic polymeric compounds is available, for example polystyrene and polymethylmethacrylate.

The degree of polymerisation of the polymer will be selected in the light of required solubility and the ability of the polymer to impart the desired properties of cohesion and viscosity to the fibreizable liquid.

We have found that generally the viscosity of the fibreizable liquid whether due solely to the presence of the fibreizable polymer or partly contributed to by the additional organic polymer should be greater than 0.1 but not greater than 150 poise. Preferably it is between 0.5 to 50 poise and more preferably between 1 and 10 poise, (viscosities being measured at low shear rates). The viscosity required using a given additional organic polymer will vary with the molecular weight of the polymer, i.e. the lower the molecular weight the higher the final viscosity needed. Again, as the molecular weight of the polymer is increased a lower concentration of it is required to give good fibreization. Thus, as examples as would mention that in the preparation of polytetrafluoroethylene mats we have found that using a polyethylene oxide of MW 100,000 as the additional organic polymer a concentration of about 12% by weight to the PTFE content is needed to give satisfactory fibreization, whereas with a MW of 300,000 a concentration of 1 to 6% may be adequate. Again, at a MW of 600,000 a concentration of 1 to 4% is satisfactory, while at a MW of $4 \times 10^6$ a concentration as low as 0.2% may give good fibreization.

The concentration of the fibreizable polymer will depend upon the amount required to provide adequate fibre properties, and will be influenced also by the need to produce a liquid of appropriate viscosity and speed of fibre hardening. Thus in the case of a dispersion we may use a concentration within the range 25% w/w to saturation, (in the case of a dispersion, 'saturation' means the maximum concentration which may be included without destroying the useful spinnability of the liquid) preferably 40 to 70% and more preferably 50 to 60%, and in the case of a solution we may use a concentration within the range 10 to 60% w/w, preferably 20 to 35% w/w.

It will be appreciated that the concentration of the components must be adjusted to take account of the presence and concentration of any other and their relative effects upon viscosity, etc.

The spinning material should have some electrical conductivity, although this may vary between quite wide limits; for example we prefer to employ solutions having conductivity within the range $1 \times 10^{-6}$ to $5 \times 10^{-2}$ mhos cm$^{-1}$.

Any convenient method may be employed to bring the spinning material into the electrostatic field, for example we have supplied the spinning liquid to an appropriate position in the electrostatic field by feeding it to a nozzle from which it is drawn by the field, whereupon fibreization occurs. Any suitable apparatus can be employed for this purpose; thus we have fed the spinning material from a syringe reservoir to the tip of an earthed syringe needle, the tip being located at an appropriate distance from an electrostatically charged surface. Upon leaving the needle the material forms fibre between the needle tip and the charged surface.

Droplets of the spinning liquid may be introduced into the field in other ways, which will be apparent to the skilled man, the only requirement being that they can be held within the field at a distance from the electrostatically charged surface such that fibreization occurs. For example they could be carried into the field on, say, a continuous carrier, e.g. a metal wire.

It will be appreciated that where the liquid is fed into the field through a nozzle, several nozzles may be used to increase the rate of fibre production. Alternative means of bringing the fibreizable liquid into the charge field may be employed, for example a perforated plate (the perforations being fed with fibreizable liquid from a manifold) may be employed.

In one embodiment the surface to which the fibres are drawn is a continuous surface, as of a drum, over which passes a belt which may be withdrawn from the region of charge, carrying with it the fibres which have been formed and which have become attached thereto. Such an arrangement is shown in the attached drawings in which FIG. 1 is a diagrammatic side view of apparatus for the continuous production of fibres. In FIG. 1, 1 is an earthed metal syringe needle supplied from a reservoir with spinning material at a rate related to the rate of fibres production. Belt 2 is of gauze driven by a driving roller 3 and an idler roller 4 to which is fed an electrostatic charge from a generator 5 (in the apparatus illustrated a Van de Graaff machine).

Removal of the fibre mat 6 from belt 1 is by any convenient means, for example by suction or by air jet, or it may be removed by juxtaposition of a second belt, or a second roller. Preferably it is cut and lifted off. In the Figure the mat is shown being picked up by a roller 7 rotating against the belt.

The optimum distance of the nozzle from the charged surface is determined quite simply by trial and error. We have found, for example, that using a potential of the order of 20 Kv a distance of 5-35 cm is suitable, but as the charge, nozzle dimensions, liquid flow rate, charged surface area etc. are varied so the optimum distance may vary, and it is most conveniently determined as described.

Alternative methods of fibre collection which may be employed include the use of a large rotating cylindrical collecting surface substantially as described, the fibres being collected from another point on the surface by a non-electrically conducting pick-up means instead of being carried away on the belt In a further embodiment the electrostatically charged surface may be the sides of a rotating tube, the tube being disposed coaxially with the nozzle and at an appropriate distance from it. Alternatively deposition of fibres and the formation of a tube may occur on a cylindrical former. The former may be made from any of a variety of materials. A metallic former is preferred and aluminium is particularly preferred. The tube may be removed from the former by a variety of methods. In particular it may be mentioned that a polyurethane tube is preferably peeled from an aluminium former while an aluminium former may be dissolved in sodium hydroxide solution to obtain a PTFE tube. To facilitate peeling the polyurethane tube from the aluminium former, the latter may be conveniently covered with a layer of flexible polyurethane foam.

The electrostatic potential employed will usually be within the range 5 Kv to 1000 Kv, conveniently 10–100 Kv and preferably 10–50 Kv. Any appropriate method of producing the desired potential may be employed. Thus, we illustrate the use of a conventional van de Graaff machine in FIG. 1 but other commercially available and more convenient devices are known and may be suitable.

It is, of course, important that the electrostatic charge is not conducted from the charged surface and where the charged surface is contacted with ancillary equipment, for example a fibre collecting belt, the belt should be made of a non-conducting material (although it must not, of course, insulate the charged plate from the material to be fibreized. We have found it convenient to use as the belt a thin Terylene (RTM) net of mesh size 3 mm wide). Obviously all supporting means, bearing etc. for the equipment will be insulated as appropriate. Such precautions will be obvious to the skilled man.

To allow high production rates, hardening of the fibres should occur rapidly and this is facilitated by the use of concentrated fibreizing liquids (so that the minimum liquid has to be removed), easily volatile solvents (for example the liquid may be wholly or partly of low boiling organic liquid) and relatively high temperatures in the vicinity of the fibre formation. The use of a gaseous, usually air, blast, particularly if the gas is warm, will often accelerate hardening of the fibre. Careful direction of the air blast may also be used to cause the fibres, after detachment, to lay in a desired position or direction. However, using conditions as described in the Examples no particular precautions were needed to ensure rapid hardening. We found that during its formaion and travel from the nozzle to the belt sufficient hardening (dehydration in the case described) occurred at ambient temperature without the need for auxiliary hardening treatment.

Mats prepared according to the present invention may be between a few microns and a few centimeters thick, the choice of thickness will depend on the particular application. Thus for a lining the thickness may be between 5 and 100 $\mu$, preferably between 10 and 50 $\mu$ and for a wound dressing the thickness may be between 25 and 1500 $\mu$, preferably between 50 and 1000 $\mu$.

The pcre size of mats prepared according to the invention may be between 0.001 and 500 $\mu$. For linings the mat should be sufficiently porous to allow penetration of cells into it, preferably the average pore dimension should be of the order of 5 to 25 $\mu$, particularly preferably between 7 and 15 $\mu$. For wound dressings the pore size will depend on the hydrophobicity of the polymer used and on the application i.e. whether adherent or non-adherent. Typical values of average pore dimension are, for an adherent polyurethane would dressing 50 to 100 $\mu$ and for a non-adherent polytetrafluoroethylene wound dressing 1 to 50 $\mu$.

The as-spun mats usually have porosities in the range 55 to 95%, which may be reduced to as low as 1% by an appropriate compressive post-treatment. The porosity will depend on the particular application, typical porosity values are, for a lining 75% and for an adherent would dressing 80% and a non-adherent wound dressing 60%. By the term porosity we mean the percentage of the total volume of the mat which is free space.

Where dispersions are employed as the spinning material, the particle size may be between 0.01 and 1$\mu$ preferably it is between 0.1 and 0.3$\mu$.

The high surface area of the mats according to the present invention affords a method of immobilising a range of active moieties so that they are constrained to act at the site of application and do not percolate throughout the body. Moieties which may be immobilised include enzymes, drugs and active carbon. These moieties may be added to the spinning solutions or dispersions or the mats may subsequently be treated with them.

While in some applications a mat of high surface area i.e. fine fibres is needed, in others a mat of high porosity is needed. Our copending British Patent Application No. 41873/74 discloses methods for obtaining a desired porosity/specific area combination, namely by addition of an electrolyte to the spinning material or by post-spinning compression of the mat.

PTFE and polyesters are the preferred polymers for non-wetting applications but we do not exclude the possibility that they be used in wettable applications after incorporation of a wettable additive. The wettable additive is preferably although not necessarily an inorganic material, conveniently a refractory material, and should have appropriate stability within the conditions of use. While the wettable additive is preferably stable to body fluids and is not leached too rapidly, if at all, we do not exclude the possibility that reaction or dissolution may not in some instances be useful or desirable. It is also obviously important that the presence of the wettable additive should not weaken the mat to such an extent that handling or use is made unduly difficult or that dimensional stability is affected to an undesirable degree. The preferred additive is an inorganic oxide or hydroxide, and examaples of such materials are zirconium oxide, titanium oxide, chromic oxide, and the oxides and hydroxides of magnesium and calcium, although any other suitable material or mixtures of such materials may be employed. Methods for incorporating a wettable additive into the mat are disclosed in our copening British Patent Application No. 41873/74.

The following Examples illustrate the invention:

EXAMPLE 1

The apparatus was as shown in FIG. 1. The belt was of "Terylene" (RTM) net 15 cm wide, the nozzle diameter was 0.25 mm, located 15 cm from the surface of the charged roll which had a diameter of 10 cm and width 16 cm.

To 80 gms of an aqueous dispersion of PTFE of number average median particle size 0.22 microns (Standard Specific Gravity of the polymer being 2.190) containing 3.6% by weight, based on the weight of the dispersion, of surfactant "Triton X100" (Rohm and Haas) and having a PTFE solids content of 60% by weight was added 20 gms of a 10% (by weight) aqueous solution of polyethylene oxide (PEO) of average molecular weight (MW) of $2 \times 5$. The final composition contained 48% by weight PTFE and about 2% by weight PEO (conductivity $1.8 \times 10^{-4}$ mhos cm$^{-1}$).

The suspension was thoroughly mixed and fed to the nozzle by an earthed syringe injector. The electrode was charged to −20 Kv and a fine jet of liquid was drawn from the nozzle and collected on the receiving surface. The fibres so collected were found to be dry and of even cross-section (1.0-2.0μ). The fibres were very friable and were removed carefully from the collector, dried at 80° C and then sintered on a bed of titanium dioxide at 380° C for 15 minutes. After this treatment the mat, 200 μ thick, was found to have retained its fibrous structure having fibres between 1 and 2 μ diameter and was quite strong.

The contact angle of the mat, measured by a modified method of Owens and Wendt, (Journal of Applied Polymer Science 1969 13 pp 1741-1747) was 137° and in the hydrostatic head test (BS 2823) a pressure of 50 cm of water failed to penetrate the mat.

A disc of the mat (1.3 cm diameter) was applied to the surfce of a wound on a rabbit involving loss of an area of full thickness skin. The rate of reepithelialisation was slightly better than that of a comparable open wound. No seepage of body fluid into the mat was observed.

The preparation was repeated to give an as-spun mat 800 μ thick, having a porosity of 83% and a pore size distribution shown in Table 1. The mat was compressed to a thickness of 300 μ for 3 min at 100° C and 400 psi and then heated at 380° C for 15 minutes. The resulting mat was 400 μ thick and had a porosity of 59% and a pore size distribution as shown in Table 2.

Table 1

| Pore Size Distribution of As-Spun Mat | |
|---|---|
| Pore Diameter (μ) | % of Pores with Smaller Diameter |
| 100 | 100 |
| 60 | 80 |
| 8 | 50 |
| 2 | 30 |

Table 2

| Pore Size Distribution of Treated Mat | |
|---|---|
| Pore Diameter (μ) | % of Pores with Smaller Diameter |
| 100 | 100 |
| 15 | 85 |
| 2.5 | 75 |
| 2 | 67 |
| 1.2 | 50 |

EXAMPLE 2

Example 1 was repeated except that 1 gm of potassium chloride was added to the spinning composition to give a conductivity of $1.2 \times 10^{-2}$ mhos cm$^{-1}$. The resulting fibers, after sintering, had diameters of 0.5-1.4.

EXAMPLE 3

Example 1 was repeated except that the polyethylene oxide had an average molecular weight of $2 \times 10^5$. The resulting fibers, after sintering, had diameters of 0.9-1.6 μ and the mat was 50 μ thick.

The contact angle of the mat, measured as in Example 1, was 123° and the mat supported a 16.5 cm column of water.

EXAMPLE 4

Figure 2:
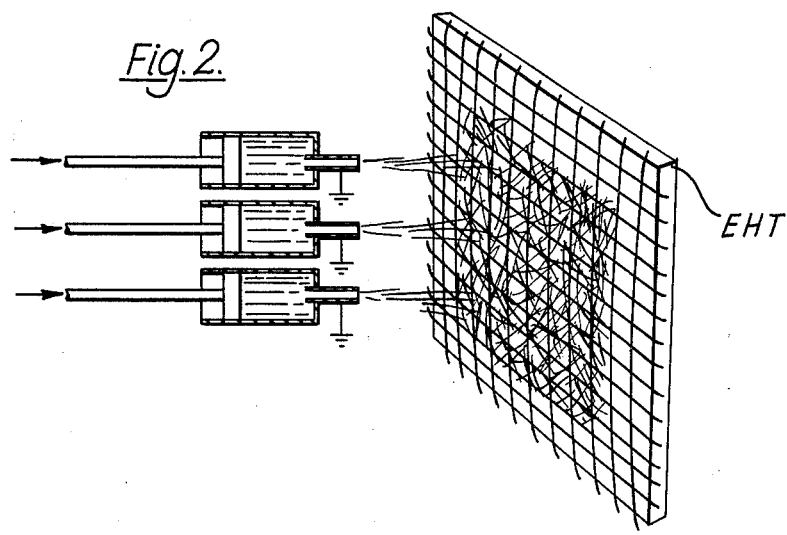
FIG. 2 is a schematic perspective view of a second embodiment of a spinning and collecting apparatus.

Example 1 was repeated except that the collecting surface was a metal gauze as shown in FIG. 2, upon which the fiber mat was supported during the subsequent sintering process.

EXAMPLE 5

Figure 3:
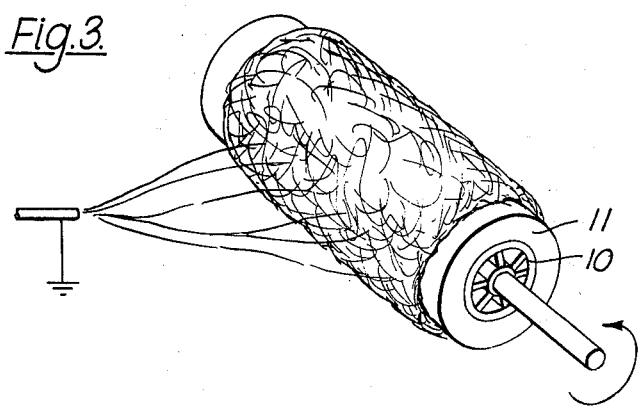
FIG. 3 is a schematic perspective view of a third embodiment of a spinning and collecting apparatus.

The process of Example 1 was repeated using a spinning solution comprising a 25% solution of a polyurethane ("Daltoflex" 330S), in dimethyl formamide/-methyl ethyl ketone (conducitivity $1 \times 10^{-6}$ mhos cm$^{-1}$) the collecting surface being a metal tube 10 having a sleeve 11 of flexible open-cell polyurethane foam (see FIG. 3), the tube being rotated at 100 rpm.

The polyurethane fibers formed had an average diameter of 2-4 microns, and were collected in the form of a tube which after completion of spinning to give a layer about 2 mm thick could be peeled from the foam.

EXAMPLE 6

The process of Example 5 was repeated except that the product was collected as a flat mat 75μ thick.

The contact angle of the mat, measured as in Example 1, was 73° and the mat supported a 1.5 cm column of water.

A portion of the mat was tested for efficacy as in Example 1. The healing wound appeared neat and tidy with the absence of any gross texture.

EXAMPLE 7

The process of Example 1 was repeated using an aluminium tubular collector having walls 0.5 mm thick, the PTFE being collected directly onto the metal. A first layer of PTFE was deposited on the collector, a close helix of Nicrome wire (0.2 mm diameter) was then applied over the PTFE, followed by another layer of PTFE fibers, and the entire composite tube, on the collector, sintered. The tube was then removed from the aluminium collector by dissolving the latter in concentrated sodium hydroxide solution.

EXAMPLE 8

The process of Example 7 was repeated using as the helical winding glass fiber of diameter 0.02 mm. Several layers of the glass fiber were employed. Tubes of diameters 1 to 10 cm have been prepared by the methods described in Examples 7 and 8.

EXAMPLE 9

A lining to a former of irregular contour was obtained by employing a porous conducting former and applying suction to the surface away from that upon which fibers were deposited sufficient to cause the fibrous mat formed to conform to the contour of the former. Such a lining could be attached to, say, an artificial body component, by use of an appropriate adhesive, e.g. nylon in formic acid or polyurethane in DMF.

EXAMPLE 10

A dust mask for pollen filtration was made by preparing a pattern shaped accurately to fit over the nose and mouth, metallising the surface of the pattern to make it adequately conducting and depositing upon the pattern a mat about 3 mm thick of polyurethane fibers which after drying could be removed from the pattern and provided an accurately contoured face mask which was both light in weight and fairly elastic.

Mats obtained generally as described in Example 1, 10 cm in diameter and having average fiber diameter 1-2 microns, average pore size 5 microns and porosity about 80% have been employed as air filters and where, the properties of the polymer are appropriate, as filters for liquids e.g. water or beer. Where the mat is of hydrophobic material, e.g. PTFE, pressure may be required to force an aqueous liquid through it. However a degree of hydrophobicity is desirable, for example where the mat is employed as a diaphragm for, say blood or other liquid oxygenation.

EXAMPLE 11

Using a cylindrical stainless steel former (1.6 cm diameter) charged to 20 Kv, a 10% solution of polyurethane ("Daltomold" 338E) in dimethyl formamide was electrostatically spun through one needle at the rate of 0.7 g of PU/hour. The tubular structure produced had a wall thickness of 0.4 mm, a total pore volume of 1800 mm$^3$/g and a median pore radius of 9.4 microns and consisted of approximately 10 micron polymer nodules cross linked together by 0.4 $\mu$ diameter fibers.

A section of this product was implanted by suturing into the descending aorta of a pig for 10 days after which the pig was killed and the graft examined. The gross findings showed it to be patent with no sign of intravascular thrombosis. Histologically, there was evidence of connective tissue and capillary ingrowth between the fibers of the prosthesis.

EXAMPLE 12

Example 1 was repeated except that a 10% by weight solution of a polyamide (Maranyl A100) in formic acid was used as the spinning material. The fibers collected were dry and had even cross-sections (0.06–0.5$\mu$).

The preparation was repeated using a 16% by weight solution of Maranyl A100 in formic. The fibers collected were dry and had even cross sections (0.70–2.8 $\mu$).

EXAMPLE 13

Example 1 was repeated except that a 12% by weight solution of polyacrylonitrile in dimethyl formamide was used as the spinning material. The fibers collected were dry and had even cross-sections (0.8–1.4 $\mu$).

EXAMPLE 14

Example 1 was repeated except that a 10% by weight solution of a polyacrylonitrile/vinylidene chloride copolymer (Viclan A85/02) in tetrahydrofuran was used as the spinning material. The fibers collected were dry and of even cross-section (1.0–2.0$\mu$).

EXAMPLE 15

Figure 4:
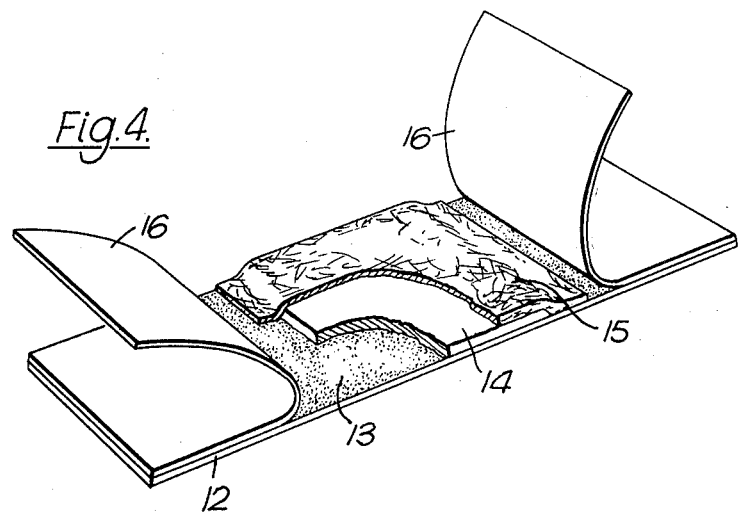
FIG. 4 is a perspective view of a wound dressing.

A wound dressing (FIG. 4) was prepared comprising a woven textile backing 12 having an adhesive surface layer 13, a pad of absorbent material 14 covered by a mat 15 of electrostatically spun material prepared as described in Example 1. The adhesive 13 of the backing is protected by cover strips 16 which are removed prior to application of the dressing.

What we claim is:

1. A lining for a prosthetic device comprising a mat of organic fibers prepared by electrostatically spinning an organic material and collecting the spun fibers on a suitable receiver.

2. A lining according to claim 1 in which the mat has an average pore size of 0.001 to 500 $\mu$.

3. A lining according to claim 1 in which the mat has a porosity between 1 and 95%.

4. A lining according to claim 1 in which the mat is of a high molecular weight fiber forming thermoplastic, a fluorinated hydrocarbon, silicone or urea/formaldehyde.

5. A lining for a prosthetic device according to claim 1, in which the thickness of the mat is between 5 and 100 microns.

6. A lining for a prosthetic device according to claim 5, in which the thickness of the mat is between 10 and 50 microns.

7. A lining for a prosthetic device according to claim 1, in which the mat has an average pore size of 5 to 25 microns.

8. A lining for a prosthetic device according to claim 1 in which the mat has an average pore size of 7 to 15 microns.

9. A lining for a prosthetic device according to claim 1 in which the mat has a porosity of 70 to 80%.

10. A lining for a prosthetic device according to claim 1 in which the mat is reinforced by a reinforcing material.

11. A lining for a prosthetic device according to claim 10 in which the reinforcing material is metallic, polymeric or glass fiber.

12. A lining for a prosthetic device according to claim 11 in which the reinforcing material is in the form of a woven or non-woven web or helix.

13. A product according to claim 1 in which enzymes, drugs or active carbon are immobilised on the surface of the fibers.

14. A product according to claim 1 in which an inorganic material is incorporated in the fibers.

15. A product according to claim 14 in which the inorganic material is an electrolyte.

16. A product according to claim 1 in which the fibers of the mat comprise polytetrafluoroethylene.

17. A lining for a prosthetic device comprising a mat formed of electrostatically spun organic fibers and having a thickness of between 5 and 100 microns, an average pore size between 5 and 25 microns and a porosity of 70 to 80%, the fibers having a diameter of 0.1 to 10 microns and being prepared by introducing a liquid containing a fiber-forming organic material into an electric field, drawing fibers from the liquid to an electrode and hardening the drawn fibers.

* * * * *